United States Patent [19]

Wizerkaniuk

[11] 4,129,666

[45] Dec. 12, 1978

[54] METHOD OF PROVIDING PELLETS WITH A WATER INSOLUBLE COATING USING A MELT

[76] Inventor: Walter Wizerkaniuk, 4146 Joshua Rd., Lafayette Hill, Pa. 19444

[21] Appl. No.: 792,461

[22] Filed: Apr. 29, 1977

[51] Int. Cl.² .................... B44C 1/08; A61K 16/28
[52] U.S. Cl. .................................. 427/3; 118/303; 118/19; 427/212
[58] Field of Search ............... 118/303, 19, 418; 427/3, 212, 242

[56] References Cited

U.S. PATENT DOCUMENTS

| | | | |
|---|---|---|---|
| 3,196,827 | 7/1965 | Wurster | 427/3 |
| 3,302,608 | 2/1967 | Coons et al. | 118/19 |
| 3,687,717 | 8/1972 | Philip | 118/303 |
| 3,798,338 | 3/1974 | Galle | 118/303 |
| 3,847,830 | 11/1974 | Williams | 428/403 |
| 3,903,333 | 9/1975 | Shirley | 118/19 |

*Primary Examiner*—Sam Silverberg

[57] ABSTRACT

Pellets may be provided with a water insoluble coating in a rotating pan by heating the pellets to a temperature of about two to three degrees centigrade below the melting point of the coating composition and subsequent thereto flowing molten coating composition onto the pellets. The method is particularly suitable for providing medicinal pellets with an enteric coating, specifically those enteric coatings having sustained release characteristics.

4 Claims, 1 Drawing Figure

U.S. Patent  Dec. 12, 1978  4,129,666
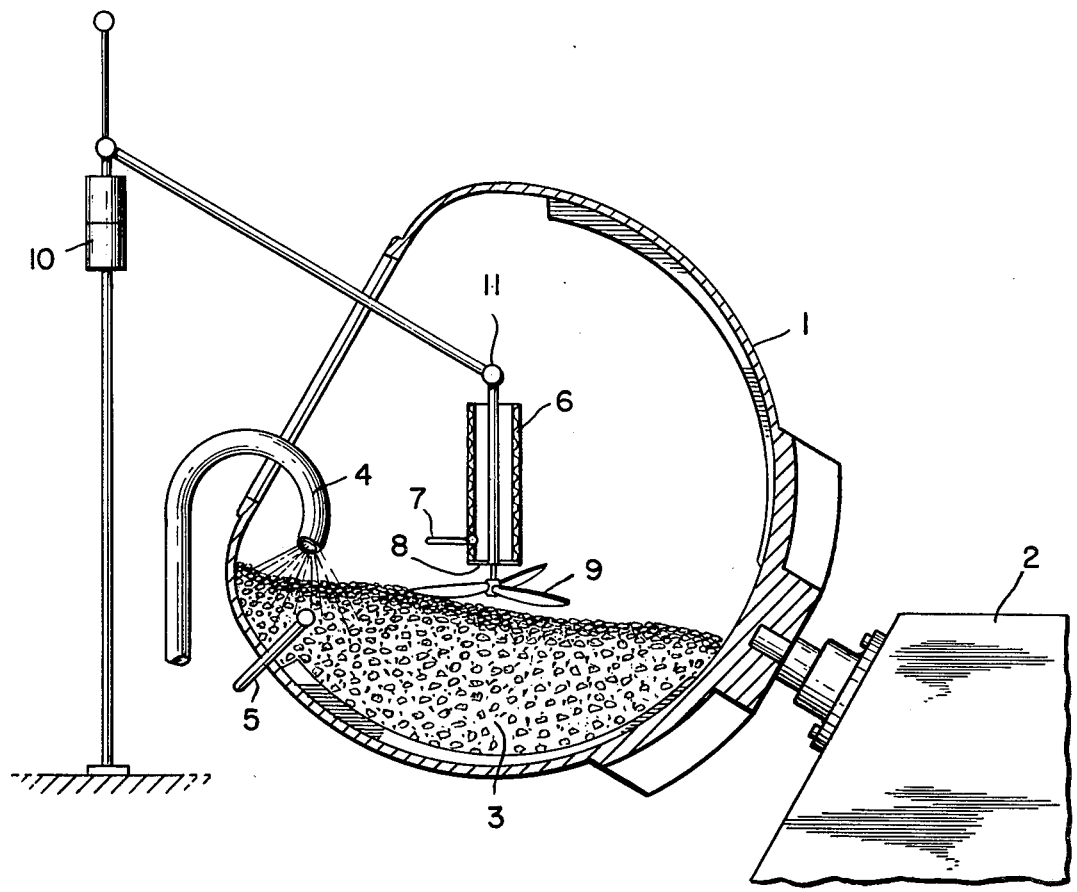

METHOD OF PROVIDING PELLETS WITH A WATER INSOLUBLE COATING USING A MELT

This invention concerns the coating of pellets with a water insoluble composition. More particularly, the invention concerns an improved method of applying an enteric coating composition to medicinal pellets by controlling the temperature of the pellets at a temperature of about two to three degrees centigrade below the melting temperature of the coating composition at the time of contacting the pellets with a flow of coating composition.

DESCRIPTION OF THE PRIOR ART

Providing medicinal pellets with an enteric coating is well known in the art. See for example, Remington Pharmaceutical Sciences, 14th edition, 1970, pages 1608-1617 and U.S. Pat. No. 3,141,792 assigned to Ciba Corporation. Although previously known coating techniques adequately coat pellets, such techniques commonly consume large amounts of organic solvents during the coating process.

Enteric coating formulations traditionally comprise "waxy" substances and are either natural in origin such as beeswax or manmade such as, for example, synthetic resins. Since medicinal coatings are most frequently sprayed, the coating compositions are normally applied in the form of their solutions in organic solvents, such as, for example, acetone, alcohol, chloroform, carbon tetrachloride and the like. Although these solvents evaporate readily and therefore, the finished coatings are obtained in a comparatively short period of time, the prior art coating processes possess many significant disadvantages:

1. Large amounts of solvents are needed as the solids content in the coating compositions used in these processes usually cannot be much more than 20% due to the viscosity requirements;
2. The solvents, which are expensive are either completely lost thereby contributing to the dangers of air pollution or can only be recovered by the use of very expensive apparatus;
3. Because of the toxicity of the solvent vapors, special safety measures must be provided in the working area in order to protect personnel;
4. Most organic solvents are flammable and mixtures of solvent vapors with air are explosive so that it is necessary to use expensive safety measures against the hazards of fire and explosion.

It has now been discovered that a process utilizing careful temperature control of the coating composition and the pellets during the coating process reduces the need for organic solvents by at least 75% and frequently 90% or more. The present process therefore avoids the disadvantages hereinabove enumerated.

It is a further advantage of the process that existing equipment such as rotating coating pans may be modified in an inexpensive manner to allow implementation of the present invention, thereby obviating the need for major capital equipment investments.

By the term pellets is meant any particles such as, for example, crystals, granules or sugar seeds which may be coated by the present invention. By the term coating as used herein, is meant a water insoluble substance which surrounds a pellet. An enteric coating is a water insoluble waxy substance surrounding a pellet which is substantially insoluble in an acid environment but which will dissolve in alkaline surroundings. A coating composition is defined as a composition useful in the practice of the invention to provide a coating onto pellets and may include minor amounts of solvent, flavoring agents, coloring agents and the like.

Although the process of the present invention is ideally suited for providing medicinal pellets with an enteric coating, its utility should not be considered limited to the coating of medicinal pellets. Any pellets which are desired to be coated by water insoluble coating may advantageously be coated by the present invention. For the purpose of illustrating the present invention however, reference is made to a process for providing an enteric coating on medicinal pellets.

SUMMARY OF THE INVENTION

According to the invention, there is therefore provided a process for providing pellets with a water insoluble coating which comprises placing the pellets in a rotating container and contacting the rotating pellets in a uniform manner with a flow of molten coating composition at a temperature such that the temperature of the pellets is maintained at about 2-3° C. below the melting temperature of the coating composition.

BRIEF DESCRIPTION OF THE DRAWING

The FIGURE shows a typical apparatus suitable for use in the process of the invention.

DETAILED DESCRIPTION OF A PREFERRED EMBODIMENT OF THE INVENTION

The general process of coating medicinal pellets with an enteric coating according to the instant invention will be explained by reference to the accompanying drawing. More specifically, the drawing shows a coating pan 1 mounted on a coating pan motor housing 2 containing standard means of rotation, a quantity of medicinal pellets to be coated 3, a warm gas supply conduit 4, a thermometer 5 to measure the temperature of the pellets, an enteric coating container equipped with heating means 6 and a thermostat 7 to control the temperature of the coating composition, the container having closeable conduits 8 to release coating composition, a rotatable propeller 9 to disperse coating onto the pellets including means 10 to raise or lower the propeller and a linkage drive 11 to rotate the propeller.

The coating procedure carried out in rotating pan 1 represents a preferred manner for carrying out the process of the invention. Thus, the medicinal pellets to be coated are introduced into a rotating angled tumbling zone of pan 1 which has been previously coated with a sugar syrup to ensure that the pellets will roll rather than slide. The enteric coating composition introduced into the container is maintained by the thermostatically controlled heating means 6 at a temperature slightly above the melting temperature of the composition. By opening closeable conduits 8, the coating composition is allowed by gravity to flow along the conductively warmed propeller shaft onto the conductively warmed rotating propeller blades. The centrifugal force exerted by the rotation of the propeller disperses the coating to the propeller tips which are positioned such that each propeller blade during its revolution will continually contact only the upper level of pellets. The pellets are maintained at a temperature of about 2-3° C. below the melting temperature of the coating composition by a warm gas supply passing through conduit 4. The temperature of the pellets may be determined by reference to thermometer 5 and adjusted by regulating either the flow of warm gas or the temperature of the gas.

A critical aspect of the invention is the temperature control of both the pellets and the coating composition. Although the temperature of the pellets should be maintained at about two to three degrees centigrade below the melting temperature of the coating composition, the temperature of the coating composition may be considerably above its melting point. Maintaining too high a temperature of the coating composition is therefore unnecessary and economically undesirable.

The thickness of the coating is primarily determined by the amount of coating composition utilized per the weight of pellets to be coated. A desirable thickness may be about 10 percent by weight of the pellet. The coating is normally applied in a uniform manner by adjusting the flow of coating composition, the rotational speed of the pan and the rotational speed of the propeller.

It should be understood that the enteric release rate of the coated pellets is primarily determined empirically. Coated pellets with different release rates are commonly mixed together to form a medicament having therefore a sustained release over a predetermined time period.

It will be appreciated that the above described apparatus is merely illustrative of how the process of the invention may be utilized. It will be readily apparent to the skilled worker in the art that many variations or modifications of the apparatus may be possible without exceeding the bounds of the invention. The apparatus is therefore to be considered representative.

The coating composition may comprise any of the waxy compositions used in the industry. Preferably however, the coating composition comprises a mixture of one or more glyceryl stearates and about 10% by weight of beeswax. Any other water insoluble ingestible wax can be substituted for beeswax. Thus, for example, Japan wax, paraffin, white wax USP, microcrystalline wax, castor wax, carnauba wax, bayberry wax, and other animal, insect, plant or other water-insoluble, non-toxic wax-like substances, such as sterols, as for example, cholesterol, are satisfactory. Any other slowly digestible or dispersible solids, such as slowly digestible fatty esters, slowly digestible fatty acids and slowly dispersible higher fatty alcohols may be used in place of glyceryl mono-di-, or tri-stearate. Thus, for example, stearic acid, palmitic acid, cetyl palmitate, diglycol stearate, glyceryl myristate, triethylene glycol monostrearate, cetyl alcohol stearyl alcohol and the like are also satisfactory. It is preferred to use solid fatty acids and alcohols having from 12 to 22 carbon atoms or esters of said solid fatty acids.

Suitable solvents include ethyl alcohol denatured with 5% methyl alcohol, chloroform and carbontetrachloride. Other suitable solvents include those commercially available under the names of Eskaysolve and Tecsolv.

Medicinal pellets useful for coating by the instant process already contain the active medicament. Active materials eligible to be contained by the enteric coating include any material which can be included as a dispersion of fine particles in a matrix binder material without dissolving or reacting therewith.

Any acid sensitive medicament substance, as a class is eligible for use, such as for example: penicillin salts, aureomycin, chloromycetin, streptomycin, bacitracin, subtilin, polymixin, dihydrosteptomycin, and other acid sensitive materials such as acetylsalicyclic insulin, adrenalin, heparin and the like. Other eligible materials include acetylsalicyclic acid, digitoxin, pyralimine, caffeine, phenobarbital, stilbesterol, methyl testosterone, scopolamine methylbromide, pentaerythritol tetranitrate, hexamethonium chloride, N-acetyl-p-aminophenol, veratrum viride, d-amphetamine sulfate, pentobarbituric acid, mephobarbital, mannitol hexanitrate, pyralimine maleate and the like. Of course, other materials physiologically active or not, acid sensitive or not, may be employed in the present invention as desired or required to a particular use. Such a use may be in controlled provisions of a catalyst or coreactant in certain pH environments or in controlled release of a dye or indicator materials under certain conditions.

The method of manufacturing medicinal pellets used in the present invention is not important and forms no part of the invention. The pellets can be manufactured by granulating a paste of matrix binder material mixed with finely divided particles of the material to be contained or by coating sucrose seeds of suitable mesh size with a medicament coating.

The pellets ready for coating with the enteric composition may have mesh sizes of broad range. Preferred mesh sizes are however from 12–40.

The following examples using the apparatus hereinabove described serve to illustrate the invention.

EXAMPLE I

Into a 24 inch coating pan previously coated with sugar syrup are placed 20 kilograms of size #18 (mesh) medicated pellets. An enteric coating composition consisting of 1,008 grams of glyceryl distearate, 672 grams of glyceryl monostearate, 168 grams of beeswax and 450 milliliters of ethyl alcohol denatured with 5% methyl alcohol is mixed and heated to 60° C. and then poured into the coating composition container where its temperature is maintained. The melting point of the composition is about 50° C. The tumbling medicinal pellets are maintained at about 47° C. in the pan which is rotating at about 90 revolutions per minute. The propeller is lowered such that each blade just touched the upper level of the rolling pellets once during each revolution. After allowing time for the propeller blades and shaft to be heated conductively by the heated coating composition, the closeable conduits of the coating composition container are opened to allow the coating composition to flow down onto the propeller blades rotating at about 200 rpm. When the container is empty, the pellets are rolled for an additional 5 to 10 minutes and then removed from the pan onto trays. The coated pellets have a smooth uniform enteric coating.

EXAMPLE II

The general procedure of Example I is repeated with an enteric coating composition consisting of 1680 grams of glyceryl distearate, 168 grams of beeswax and 200 milliliters of ethyl alcohol denatured with 5% methyl alcohol and having a melting point of about 52° C. The pellets so coated have a smooth uniform enteric coating.

EXAMPLE III

The general procedure of Example I is repeated with an enteric coating composition consisting of 1700 grams of glyceryl distearate and having a melting point of about 58° C. The pellets so coated have a smooth uniform enteric coating.

EXAMPLE IV

The general procedure of Example I is repeated with an enteric coating composition consisting of 1008 grams of glyceryl distearate, 672 grams of glyceryl monostearate and 168 grams of beeswax and having a melting point of about 56° C. The pellets so coated have a smooth uniform enteric coating.

What is claimed is:

1. A process for enterically coating medicinal pellets in a rotating coating pan equipped with a rotatable propeller having a substantially vertically disposed shaft, means for controlling the temperature of the pellets when disposed in the coating pan and a coating composition container equipped with heating element, temperature control and closeable conduit to release molten coating composition from the container onto the shaft which process comprises;

(a) placing the pellets into the rotating pan and adjusting the position of the propeller such that each propeller blade during its revolution will continually contact only the upper level of the pellets, (b) maintaining the pellets at a temperature of about 2°-3° C. below the melting temperature of the coating composition, (c) dispersing the coating composition onto the pellets in a uniform manner by releasing molten coating composition from the container through the closeable conduit to flow down the propeller shaft onto and over the rotating propeller blades and onto the pellets, (d) rotating the pan to obtain a uniform coating on each pellet.

2. A process as claimed in claim 1 wherein the rotating pan rotates at about 90 revolutions per minute and wherein the propeller rotates at about 200 revolutions per minute.

3. A process as claimed in claim 1 wherein the coating composition comprises from about 0 to 25 percent by weight of an organic solvent.

4. A process as claimed in claim 1 wherein the pellets have a mesh size of from about 12 to 40.

* * * * *